United States Patent [19]

Sugai et al.

[11] 4,209,293
[45] Jun. 24, 1980

[54] AIR BEARING FOR A DENTAL HANDPIECE

[75] Inventors: Hiroshi Sugai; Shoji Nakayama, both of Kyoto, Japan

[73] Assignee: Kabushiki Kaisha Morita Seisakusho, Kyoto, Japan

[21] Appl. No.: 884,596

[22] Filed: Mar. 8, 1978

[30] Foreign Application Priority Data

Mar. 8, 1977 [JP] Japan ................................. 52-25765

[51] Int. Cl.$^2$ ............................................... A61C 1/12
[52] U.S. Cl. ................................................... 433/132
[58] Field of Search ............. 32/27, DIG. 1; 415/503; 433/132

[56] References Cited

U.S. PATENT DOCUMENTS

| | | | |
|---|---|---|---|
| 3,055,112 | 9/1962 | Borden | 32/DIG. 1 |
| 3,384,344 | 5/1968 | Ota | 415/503 |
| 3,408,043 | 10/1968 | Williams et al. | 32/27 |
| 3,962,789 | 6/1976 | Flatland | 32/27 |

Primary Examiner—Louis G. Mancene
Assistant Examiner—John J. Wilson
Attorney, Agent, or Firm—Koda and Androlia

[57] ABSTRACT

This invention relates to a driving mechanism of an air bearing journaled handpiece for dental treatment, the mechanism being improved in that even when a load contrary to the direction of rotation of a tool shaft such as cutting of the teeth acts upon the tool shaft in a dental operation, rotation of the tool shaft does not stop because of load resistance but enables the heretofore, unmaterialized medium-speed cutting (hereinafter referred to as "extension to medium-speed rotation") and makes it possible to obtain improved torque during high-speed rotation in addition to the extension to medium-speed rotation.

8 Claims, 9 Drawing Figures

AIR BEARING FOR A DENTAL HANDPIECE

BACKGROUND OF THE INVENTION

1. Field of the Invention

This invention relates to a dental handpiece of an air-driven turbine operated and air bearing journaled type (the type wherein a trubine rotor is journaled in air bearings in the radial and thrust directions) and more particularly to a dental handpiece improved in its cutting ability during medium-speed rotation of a turbine and increased in torque during high-speed rotation of the turbine.

2. Description of the Prior Art

Needless to say, the highly desirable requirement of the handpiece of the kind described is to finish cutting work in a short time and without giving pain to a patient. However, a wide range of speed from superhigh speed of 550,000 rpm to low speed of 100,000 rpm is demanded in the tooth cutting and a conventional type air bearing journaled handpiece is readily adaptable for the superhigh-speed rotation because of its internal mechanism and appearance and shape, but is not suited for medium-speed rotation, with the result that sufficient cutting ability is not obtained insofar as the medium-speed rotation is concerned and recourse must be had to a ball bearing type or an electrically operated micrometer type if it is desired to obtain sufficient cutting ability for medium-speed rotation.

SUMMARY OF THE INVENTION

Accordingly, this invention has for its object the provision of a driving mechanism which can be introduced into an air-turbine operated and air bearing journaled type handpiece and which is capable of cutting both at superhigh-speed and at medium-speed rotation, and is directed to the improvements menthoned above.

According to the invention, one handpeice can sufficiently provide both superhigh-speed cutting of 550,000 rpm and low-speed cutting of 100,000 rpm. This fact makes a striking contrast to the conventional type handpiece in which, as will become apparent from a later description, rotation slows down suddenly from about 350,000 rpm and stops when a reverse load applied to the handpiece increases above 100 g.

The technical means of the invention to obtain the above object includes working out very simple partially receding surface portions on the end faces opposing the thrust gaps of a pair of forward and rearward bearings (readjustment of the bearing member side) and working out simple cutouts in in each of the turbine blades in addition to the partially receding surface portions and the extension to medium-speed rotation is obtained by the former's working and increased torque in high-speed rotation is also obtained by the combined use of the latter's working. Accordingly, special mention must also be made of the advantage that the invention can achieve the object mentioned above without involving any complicated mechanism but by employment of a very simple mechanism.

BRIEF DESCRIPTION OF THE DRAWINGS

The above mentioned features and objects will become more apparent from the following description taken in conjunction with the accompanying drawings wherein like reference numerals indicate like elements and in which.

DETAILED DESCRIPTION OF THE INVENTION

Figure 1:
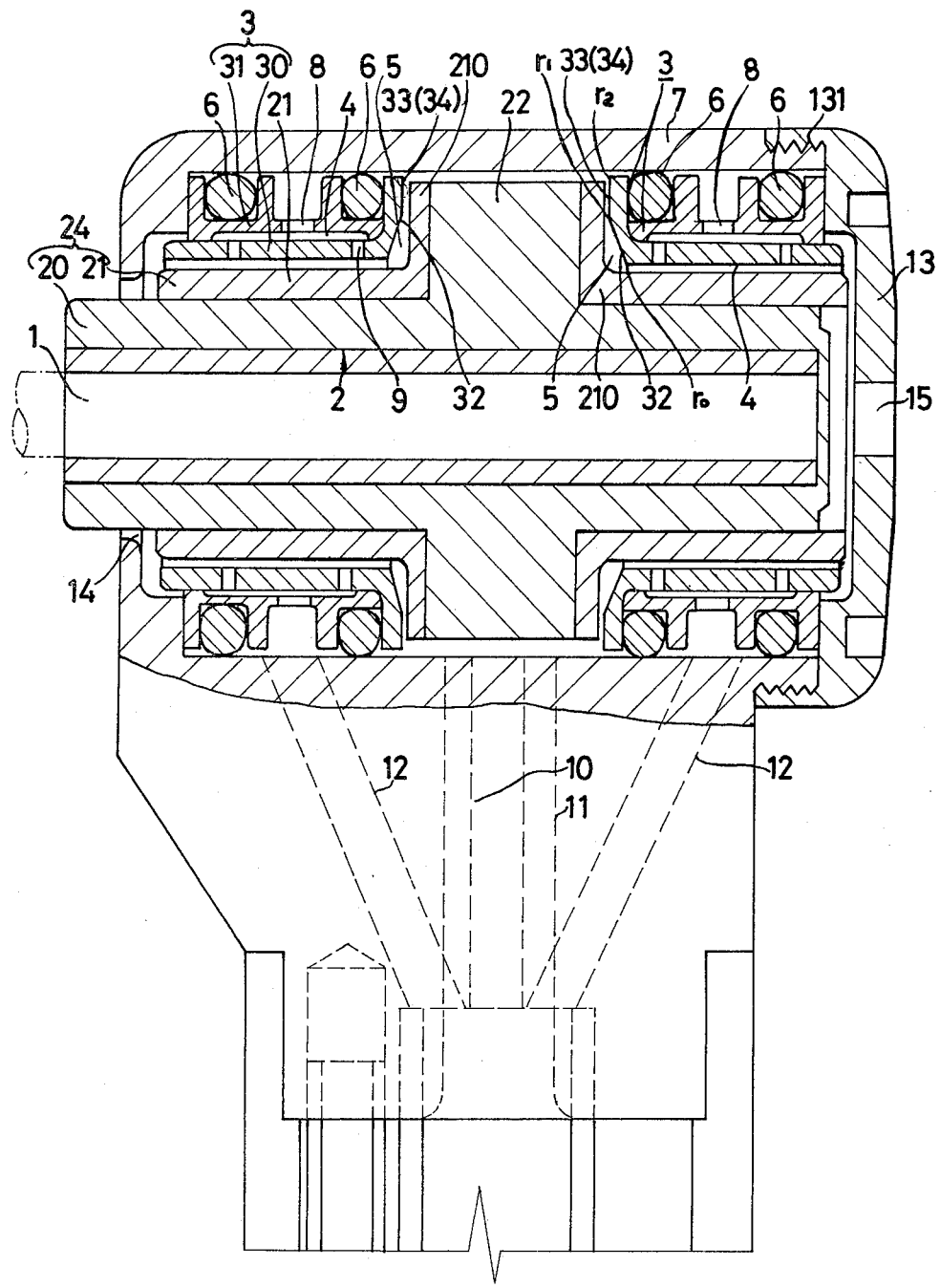
FIG. 1 is a longitudinal sectional front view of a handpiece showing a first embodiment of the invention.

Before explaining the characteristic structure of the first and the second embodiment, a brief description will now be given of a mechanism common to the embodiments. The numeral 1 designates a cutting tool shaft which is supported by a shaft unit 24. More particularly, the shaft unit 24 comprises a shaft 20 of a turbine rotor 2 and a shaft sleeve 21 sheathed over the shaft 20. The numeral 3 designates a bearing unit having radial gaps 4 provided spacedly with respect to the shaft unit 24 and thrust gaps 5 provided spacedly with respect to a vertical flange 210 formed at the end of the shaft 21 and comprising inner and outer races 30 and 31, the bearing unit being fixed to a case 7 by pressing O-rings 6 between the outer race 31 and the inner circumference of the case 7. The bearing unit incudes air feed holes 8 and 9 for feeding air to the gaps 4 and 5. The numeral 10 designates an air feed passage to turbine blades 22; 11 an air exhaust passage; 12 an air feed passage to the bearing unit 3; 13 an end lid covering the case by a screw thread 131; and 14 and 15 designate respectively exhaust passageways from the bearing unit 3. It is well known in a handpiece of this kind that compressed air supplied from the feed passages 10 and 12 by the structure is in charge of driving of the turbine blades and of the radial and thrust air bearing in the gaps 4 and 5. Indicentally, the above description has been given of only one of the pair of shaft units provided forwards and rearwards in the thrust direction of the tool shaft 1, but the other is also of the same structure.

First Embodiment

Figure 2:
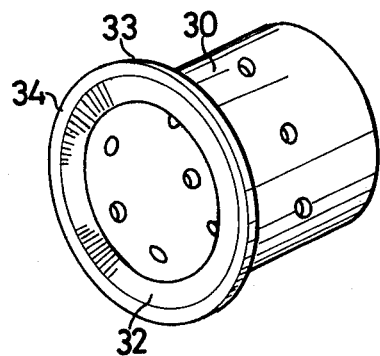
FIG. 2 is an enlarged perspective end view of a bearing unit of the handpiece.

The structure in the first embodiment is characterized in that partially receding surface portions 32 and 32 substantially enlarging centripetally the thrust gaps 5, 5 of the pair of forward rearward shaft units 3, 3 are provided respectively on the end faces 33 and 33 opposed to the thrust gaps 5, 5. In FIGS. 1 and 2 these partially receding surface portions 32, 32 are shown as a preferred example in which vertical portions 34, 34 (i.e., portions left not receding but vertical) are left on each radial end side of the ends 33, 33 and the partially receding surface portions are provided by forming slantingly cut portions opposed to L-shaped bent portions of flanges 210, 210 of the shaft sleeves 21, 21 respectively.

Figure 7:
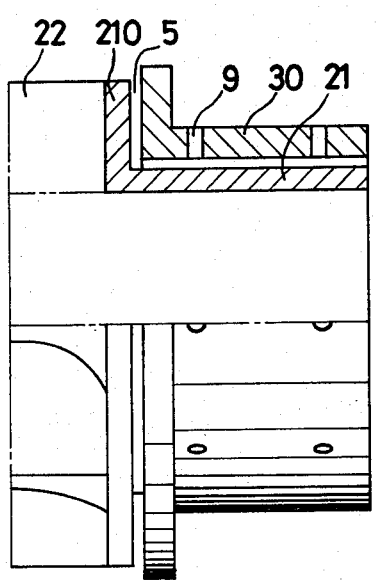
FIG. 7 shows, partly in section, a relation between the conventional turbine rotor and the bearing unit.
Figure 8:
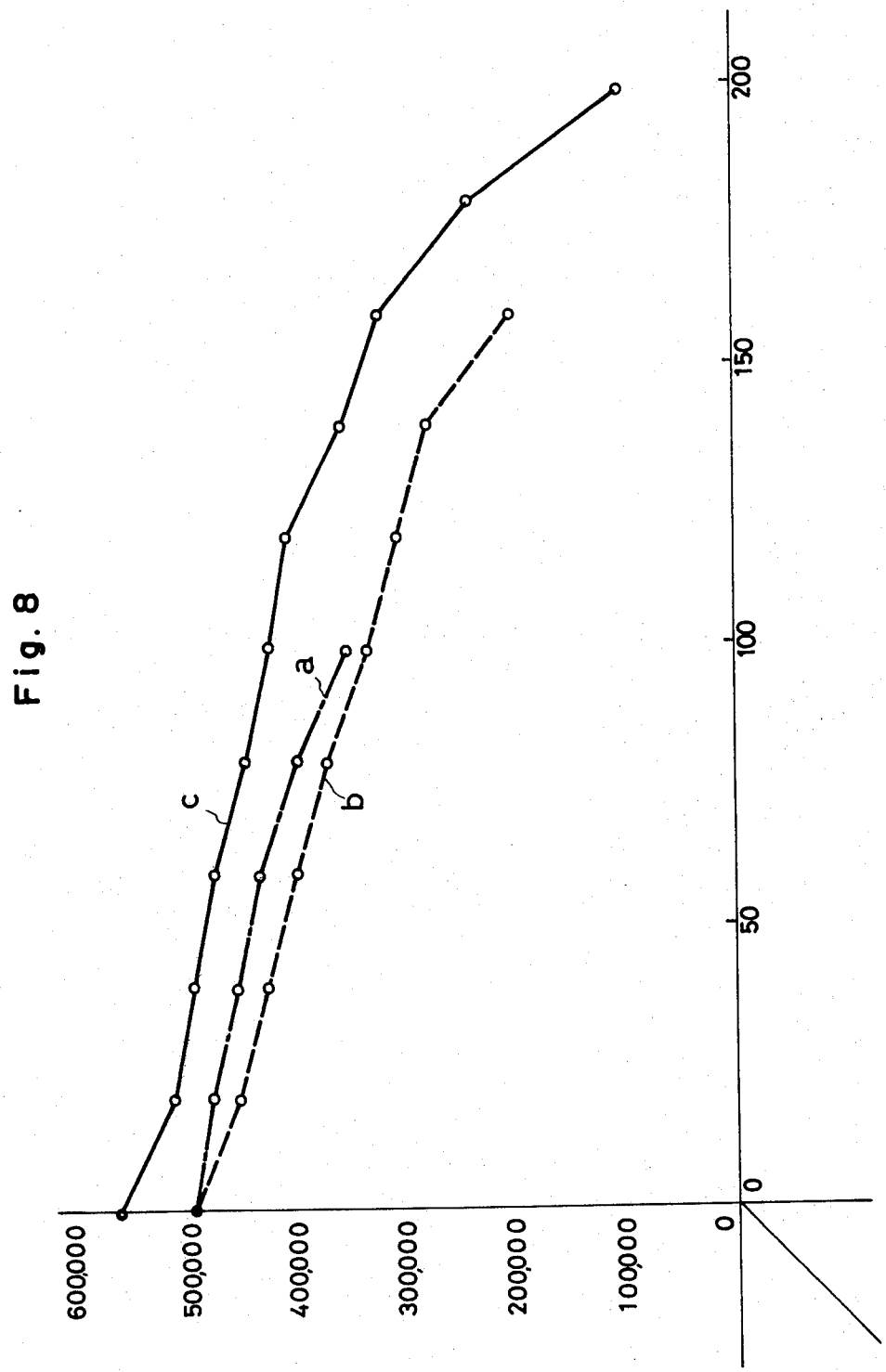
FIG. 8 is a diagram showing the cutting characteristics of the handpiece of the invention and of the conventional type.

In contrast thereto, the ends 33, 33 of the conventional bearing units 3, 3 as shown in FIG. 7 form vertical walls with respect to their entire length and have no substantial enlargement with respect to centripetal gaps between opposing turbine blades 22 respectively. As will become apparent from a later description, the extension to medium-speed rotation is obtained by provision of the partially receding surface portions 32 and 32. To explain this graphically in FIG. 8, the curves in the diagram show a relation between the reverse load applied to the tool shaft and the number of rotations of the tool shaft responsive to a change in the load applied to the shaft. The curve a indicates a curve illustrative of the same relation concerning the prior art mechanism in FIG. 7 and as apparent from the diagram shown in FIG. 8, the prior art mechanism shows the number of rotation of 350,000 rpm under a load of 100 g and shows that when the load exceeds such load, the tool shaft suddenly stops rotating. In contrast thereto, the curve b according to the first embodiment shows that although the number of rotations of the tool shaft becomes smaller about 200,000 rpm with respect to a load of 0–100 g than the curve a, the shaft can continue cutting up to a stage wherein the load esceeds 150 g. Namely, the curve b shows that extension in the medium-speed area is assured. And the reduction in cutting ability which the above decrease in the number of rotations signifies is about 5 percent, and when this amount of decrease is compared with the extension in medium-speed, the reduction may be small enough to be ignored. The test in FIG. 8 shows the case in which a reverse load is applied to a cutting tip by contact with metal therewith in the same manner as the case in which a reverse load is applied to a cutting tip by cutting of teeth carried out at a dentist's office.

Figure 3:
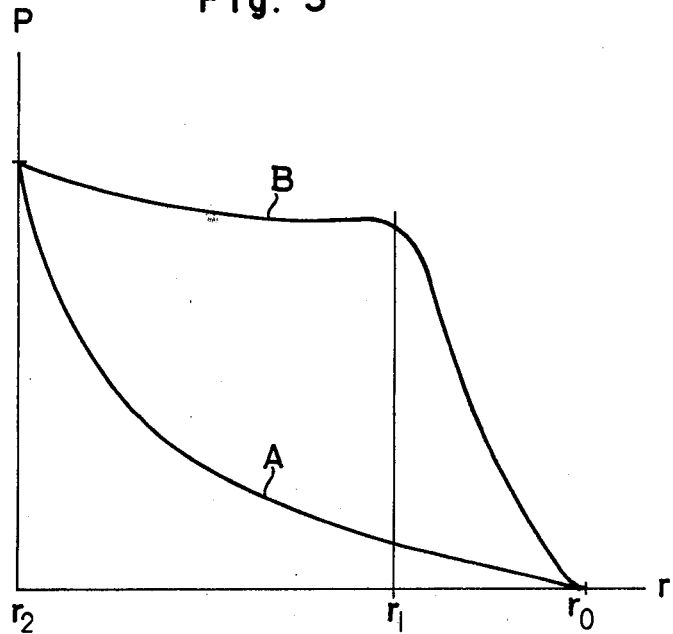
FIG. 3 shows pressure distribution curves in the thrust gaps respectively of the first embodiment bearing and of the conventional type bearing.

The following pressure distribution may be mentioned for example as the reason for the above characteristics of the first embodiment. FIG. 3 shows the conventional mechanism (one in FIG. 7) and the mechanism in the first embodiment. Namely, FIG. 3 shows graphically the result of calculation of pressure distribution within the thrust gaps 5 in the state of no rotation, and in the figure, axis of abscissa r shows a distance (position) from the inside end $r_0$ of the bearing end face 33 shown in FIG. 1 toward a radial outside end $r_2$ including a stepped portion $r_1$ relative to the partially receding surface portion 32, and the axis of ordinate p shows pressure which corresponds to each position it takes. In the case of the conventional type handpiece, the curve A shows that the pressure within the thrust gaps 5 is reduced in a greater degree in a reverse ratio at the inside end $r_0$ than at the outside end $r_2$ and leaves no reserve of pressure. In contrast thereto, the curve B in the first embodiment shows that little or no decrease is made from the outside end $r_2$ to the stepped portion $r_1$ but high pressure is maintained and pressure drops suddenly from beginning of the stepped portion $r_1$ to the inside end $r_0$. But the curve B maintains overwhelmingly higher pressure even in this range of sharp reduction than the curve A. In other words, the first embodiment shows that the radial pressure distribution within the thrust gaps in the embodiment is aboslutely higher than that in the conventional type handpiece. It was accepted that this theoretical graph is very similar to actual pressure graph.

Accordingly, it is apparent from the above fact that the load carrying capacity of the thrust part, namely the value obtained from integration of the pressure distribution in terms of area over the whole thrust surface is far higher in the handpiece of the first embodiment than in the handpiece of the conventional type. The load carrying capacity in the direction of thrust is useful for keeping the balance of the bearing 3 and rotor 2, and the balance thus kept may be said to appear in the form of extension to medium-speed.

Second Embodiment

Figure 4:
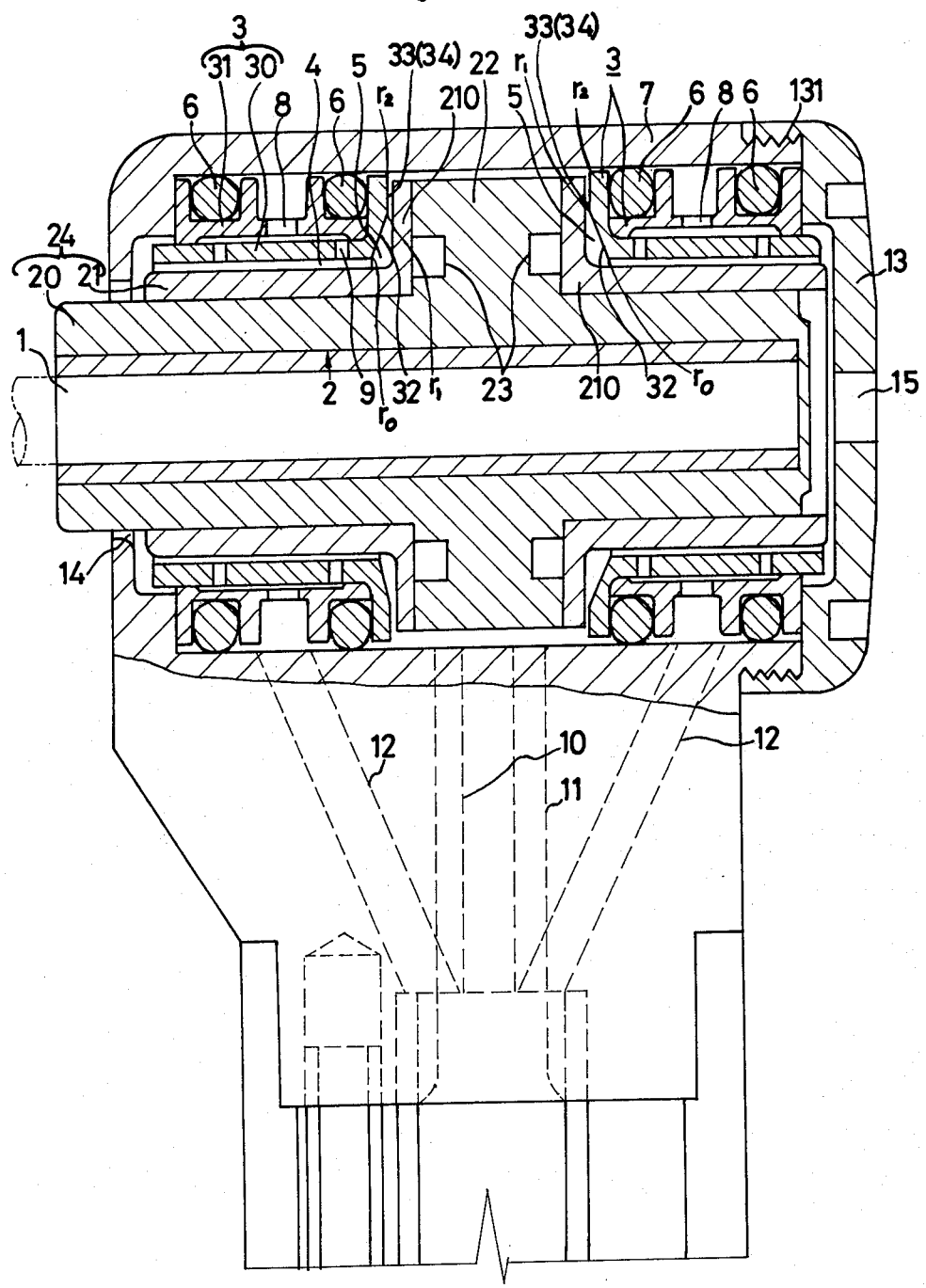
FIG. 4 is a longitudinal sectional view of a second embodiment.
Figure 5:
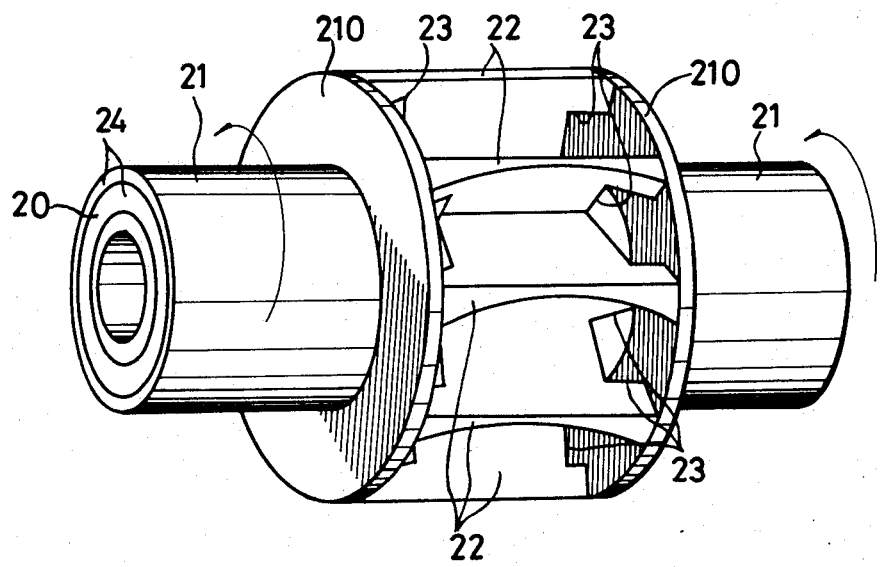
FIG. 5 is an enlarged perspective view exclusively of a turbine rotor of the second embodiment in FIG. 4.
Figure 6:
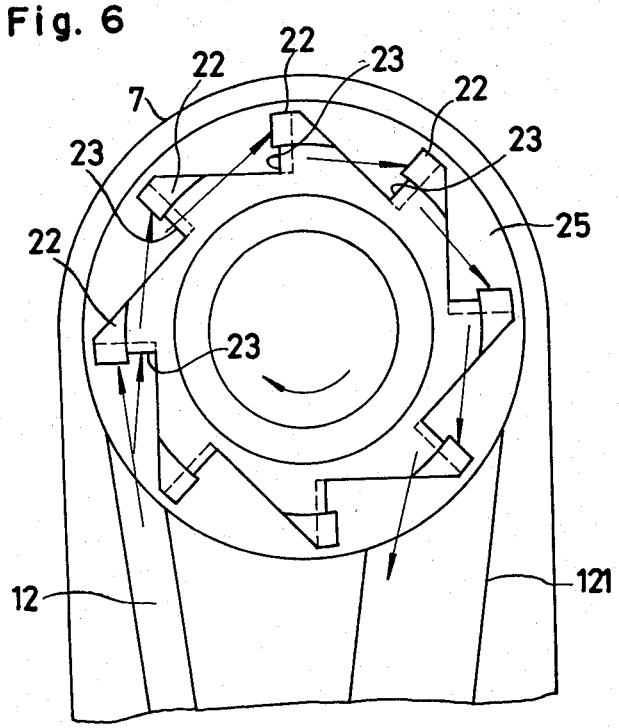
FIG. 6 is a view explanatory of an air passageway in the rotor in FIG. 5.

The structure of the second embodiment is the one in which the following new structure is added to turbine blades 22 in combination with the shaft units 3, 3 of the first embodiment. Namely, as shown in FIGS. 4 and 5, cutout openings 23, 23 are formed at both thrust-directed balde ends of the turbine blades 22, and the openings 23, 23 illustrated are shown as longitudinally rectangular cutout grooves formed on the inside of the blade ends. According to this structure, as shown in FIG. 6, the air supplied under pressure from an air feed passage 12 into a rotor blade chamber 25 comes into collision with blades 22 one after another to thereby rotate the blades and to pass in part successively through the cutout openings 23 arranged circumferentially interruptedly and communicatingly with each other and form a continuous air flow passage in exhaust passageway 121. It is well known that, in the turbine mechanism of the kind described, most of the air that collided with the turbine blades 22 turned toward the inner circumferential wall side of a case 7 and part of momentum at this time becomes torque of the blades 22, but because in the conventional mechanism the turbine blades 22 are generally of blind structure, the air that changed its direction after the aforesaid collision with the turbine blades 22 collides heavily with the inner circumference of the case 7 and in consequence of the consumption of the momentum by friction produced in the collision with the inner circumference of the case, energy that gives birth to the torque of the blades 22 is reduced to thereby decrease cutting ability. In contrast thereto, according to the second embodiment, because part of air escapes from the cutout opening 23 and collides with the turbine blades 22 successively positioned in the direction of rotation one after another, frictional losses due to the case 7 becomes small to thereby make it possible to improve the torque of the rotor.

The curve c in FIG. 8 shows a cutting characteristic of the second embodiment. According to the characteristic, the bearing mechanism of the second embodiment provides a very great advantage distinguishable from the cutting ability of the conventional mechanism in that the former makes cutting possible not only at such a heretofore unavailable high-speed rotation as 550,000 rpm but also in a low-speed rotation such as 100,000 rpm.

The description has been given of embodiments representative of this invention, but it is to be understood that various modifications such as following could be made without departing from the spirit of the invention.

(1) In the first embodiment, the partially receding surface portions 32 are formed not partially but entirely over the whole surface from the radial outside end $r_2$ to the inside end $r_0$ of the end face 33.

Figure 9:
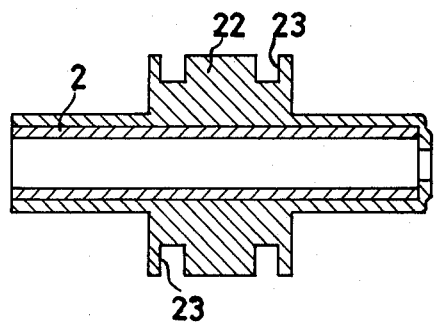
FIG. 9 is a longitudinal sectional front view showing another aspect of the turbine blade in the second embodiment.

(2) In the second embodiment, through holes are formed instead of the cutout grooves and, as shown in FIG. 9, the holes are formed on the outside of both blade ends of the blades. In this case also, the air that flows out from the cutout openings 23 threads its way axially through the turbine and works in the same manner as in FIG. 6.

Having described our invention as related to the embodiments shown in the accompanying drawings, it is our intention that the invention be not limited by any of the details of description, unless otherwise specified, but rather be construed broadly within the spirit and scope as set out in the appended claims.

We claim:

1. An air bearing journaled handpiece for dental treatment having a turbine rotor chucking and cutting tool shaft journaled by bearing units having a pair of forward and rearward thrust gaps and radial gaps provided therein and a driving mechanism for said air bearing journaled handpiece, said handpiece being characterized by partially receding surface portions substantially enlarging said thrust gaps centripetally with respect to the rotational axis of said shaft respectively provided on end faces opposing the thrust gaps of said bearing units, whereby the radial pressure distribution within said thrust gaps is substantially increased.

2. A driving mechanism of an air bearing journaled handpiece for dental treatment according to claim 1 wherein each of said partially receding surface portions is formed partially of the end face of said bearing unit and leaves a part of a vertical wall as it is.

3. A driving mechanism of an air journaled handpiece for dental treatment according to claim 1 wherein each of said partially receding surface portions are formed at least partially of the end face of said bearing unit.

4. An air bearing journaled handpiece for dental treatment having a turbine rotor chucking a cutting tool shaft journaled by bearing units having a pair of forward and rearward thrust gaps and radial gaps provided therein and a driving mechanism for said air bearing journaled handpiece, said handpiece being characterized by partially receding surface portions substantially enlarging said thrust gaps centripetally with respect to the rotational axis of said shaft respectively provided on end faces opposing the thrust gaps of said bearing units and by cutout openings formed in both blade end portions in the respective thrust directions of turbine blades of said turbine rotor whereby the radial pressure distribution within said thrust gaps is substantially increased.

5. A driving mechanism of an air bearing journaled handpiece for dental treatment according to claim 4 wherein each of said partially receding surface portions is formed partially of the end face of said bearing unit and leaves a part of a vertical wall as it is.

6. A driving mechanism of an air bearing journaled handpiece for dental treatment according to claim 4 wherein each of said partially receding surface portions is formed at least partially of the end face of said bearing unit.

7. A driving mechanism of an air bearing journaled handpiece for dental treatment according to claim 4 wherein said cutout openings are cutout grooves.

8. A driving mechanism of an air bearing journaled handpiece fo dental treatment according to claim 4 wherein said cutout openings are through holes.

* * * * *